United States Patent [19]

Bailey et al.

[11] Patent Number: 5,525,707
[45] Date of Patent: Jun. 11, 1996

[54] N-TERMINAL PEPTIDE DEGRADATION UTILIZING DIALKYLTHIOCARBAMOYLHALIDES

[75] Inventors: Jerome M. Bailey, Duarte; John E. Shively, Arcadia, both of Calif.

[73] Assignee: City of Hope, Duarte, Calif.

[21] Appl. No.: 146,161

[22] PCT Filed: Mar. 16, 1992

[86] PCT No.: PCT/US92/02162

§ 371 Date: Nov. 15, 1993

§ 102(e) Date: Nov. 15, 1993

[87] PCT Pub. No.: WO93/19083

PCT Pub. Date: Sep. 30, 1993

[51] Int. Cl.[6] .............. C07K 1/00; C07K 1/107; C07K 1/113; G01N 33/48
[52] U.S. Cl. .............. 530/345; 530/408; 562/875; 436/89
[58] Field of Search .............. 530/345, 408; 562/875; 436/89

[56] References Cited

U.S. PATENT DOCUMENTS 5,270,213 12/1993 Farnsworth .............. 436/89

OTHER PUBLICATIONS

Streitwieser et al Introduction to Organic Chemistry pp. 157–183 1985.

Primary Examiner—Christina Y. Chan
Assistant Examiner—Nancy J. Degen
Attorney, Agent, or Firm—Rothwell, Figg, Ernst & Kurz

[57] ABSTRACT

An N-terminal peptide sequencing method is disclosed in which a thiocarbamoyl compound is reacted with N-terminal amino acid of the sample to form a derivative of said amino acid which is then cleaved.

4 Claims, 1 Drawing Sheet

N-TERMINAL PEPTIDE DEGRADATION UTILIZING DIALKYLTHIOCARBAMOYLHALIDES

This invention was made with government support under Grant No. GM46022 awarded by the National Institutes of Health. The government has certain rights in the invention.

FIELD OF THE INVENTION

This invention relates to the sequential degradation of proteins and peptides from the N-terminus. More particularly, the invention relates to the sequential N-terminal degradation of peptides, including small peptide samples utilizing a novel reagent which facilitates identification of the released amino acids by mass spectrometry or fluorescence.

BACKGROUND OF THE INVENTION

Proteins are linear chains of twenty covalently linked naturally occurring amino acids. The amino acid sequence or primary structure determines the manner in which the chain can fold to form the secondary and tertiary structures necessary for biological function. When only smaller quantities of a rare protein are isolated sequence analysis is an essential prerequisite to cloning.

Currently, protein sequence analysis is primarily accomplished with the use of an automated sequencer using chemistry developed by Edman over 40 years ago (Edman, *Acta Chem. Scand.* 4:283–293 (1950)). Since that time improvement in the instrumentation has resulted in the ability to sequence smaller and smaller sample quantities (mmole to pmol), although the original chemistry has remained essentially unchanged. Current automated instrumentation permits 10–20 cycles of sequence determination on 10–50 pmol of sample (Simpson, et al., *Anal. Biochem.* 177:221–236 (1989)).

Advances in protein isolation methodology have recently made it possible to isolate sub-picomole quantities of proteins of biological interest which are present in tissues. Improved methods of protein sequencing requiring less sample quantity would make it possible to obtain the necessary sequence information in order to clone and express these proteins, and hence to study the structure function aspects thereof. These proteins often have key roles in the development and treatment of human disease.

The major limitation of Edman chemistry is the practical detection limit of the peptidylthiohydantoin (PTH) amino acids. The current method involves separation of the PTH amino acids by high-performance liquid chromatograph (HPLC) using UV detection. The practical detection limit of this method is approximately 1 pmol. A number of methods have been proposed to increase the sensitivity of Edman degradation by the use of radiolabeled, chromophoric, or fluorescent isothiocyanate reagents. 4-(N,N'-Dimethylamino)azobenzene-4'-isothiocyanate (DABITC), a highly chromophoric reagent, was introduced by Chang (Chang, et al., *Biochem. J.* 153:607–611 (1976)). Fluorescent reagents, such as fluorescein isothiocyanate (Maeda, et al. *Biochem. Biophys. Res. Commun.* 31:188–192 (1968); Muramoto, K., et al. *Anal. Biochem.* 141:446–450 (1984)), and dansyl-containing isothiocyanates (Hirano, et al. *Biol. Chem. Hoppe-Seyler* 164:257–263 (1986); Hirano, et al. "Methods in Protein Sequence Analysis" (Ed. B. Wittman-Liebold) Springer-Verlag, Berlin, pp. 42–51 (1986); Jin, S. W., et al. *FEBS Lett.* 198:105–154 (1986); Jin, S. W., et al., In: Methods in Protein Sequence Analysis (Ed. B. Wittman-Liebold) Springer-Verlag, Berlin, pp. 34–41 (1989); Sainikow, J., et al. In: Methods in Protein Sequence Analysis (Ed. K. A. Walsh) Humana Press, Clifton, N.J., pp. 247–260 (1987)) have also been evaluated as sensitivity enhancing reagents. Although synthetically prepared amino acid analogues prepared using these reagents have shown subpicomole sensitivity by HPLC analysis, in automated sequencing the sensitivity of the standard Edman methodology has not been surpassed. It is postulated that the large chromophore of such reagents may interfere with the derivatization and cleavage reactions of the Edman degradation. The use of radiolabeled reagents has failed consequent from autoradiodegradation which results in decreasing product yields and increasing amounts of labeled by-products.

An alternative method has more recently been proposed which involves treatment of the anilinothiazolinone (ATZ) derivative normally formed in Edman chemistry with a fluorescent amine (Tsugita, A., et al., *J.Biochem.* 106:60–65 (1989)). The advantage of this approach is that the derivatization and cleavage reactions of the Edman chemistry remain unchanged. Theoretically this chemistry should permit sequencing on femtomole levels of sample. However, investigation of this has revealed a number of problems which tend to defeat the goal of more sensitive sequencing. Foremost is the instability of the ATZ-amino acids which are required for reaction with the fluorescent amine. The ATZ-amino acids, in particular the hydrophilic amino acids such as histidine, glutamate, and aspartate, were found to rearrange to the PTH derivative so rapidly that reaction with the fluorescent amine was not possible.

A possible solution to this problem is to convert the PTH amino acid back to the ATZ amino acid so that reaction with the fluorescent amine will be possible. The aminolysis of PTH amino acids is discussed in detail by Pavlik, et al., *Anal. Biochem.* 201:9–16 (1992). Replacement of the fluorescent amine with a reagent such as N,N-dimethylethylenediamine (DMED) has been found to permit detection in the femtomole level using electrospray mass spectrometry. The introduction of the tertiary amine to the amino acid derivative was found to enhance detection of the amino acid by 25 times as compared to the PTH-amino acid, thereby making mass spectrometry a viable method for enhancing the levels of detection during protein sequencing.

SUMMARY OF THE INVENTION

This invention entails the utilization of certain thiocarbamoyl compounds as coupling reagents in the sequential degradation of proteins and peptides from the N-terminus. The methods of the invention are readily automated using presently available instrumentation. When practiced in conjunction with fluorescent or mass spectral detection methods, the invention permits the N-terminal sequence determination of sample quantities in the sub-picomole range.

DETAILED DESCRIPTION OF THE INVENTION

Figure 1:
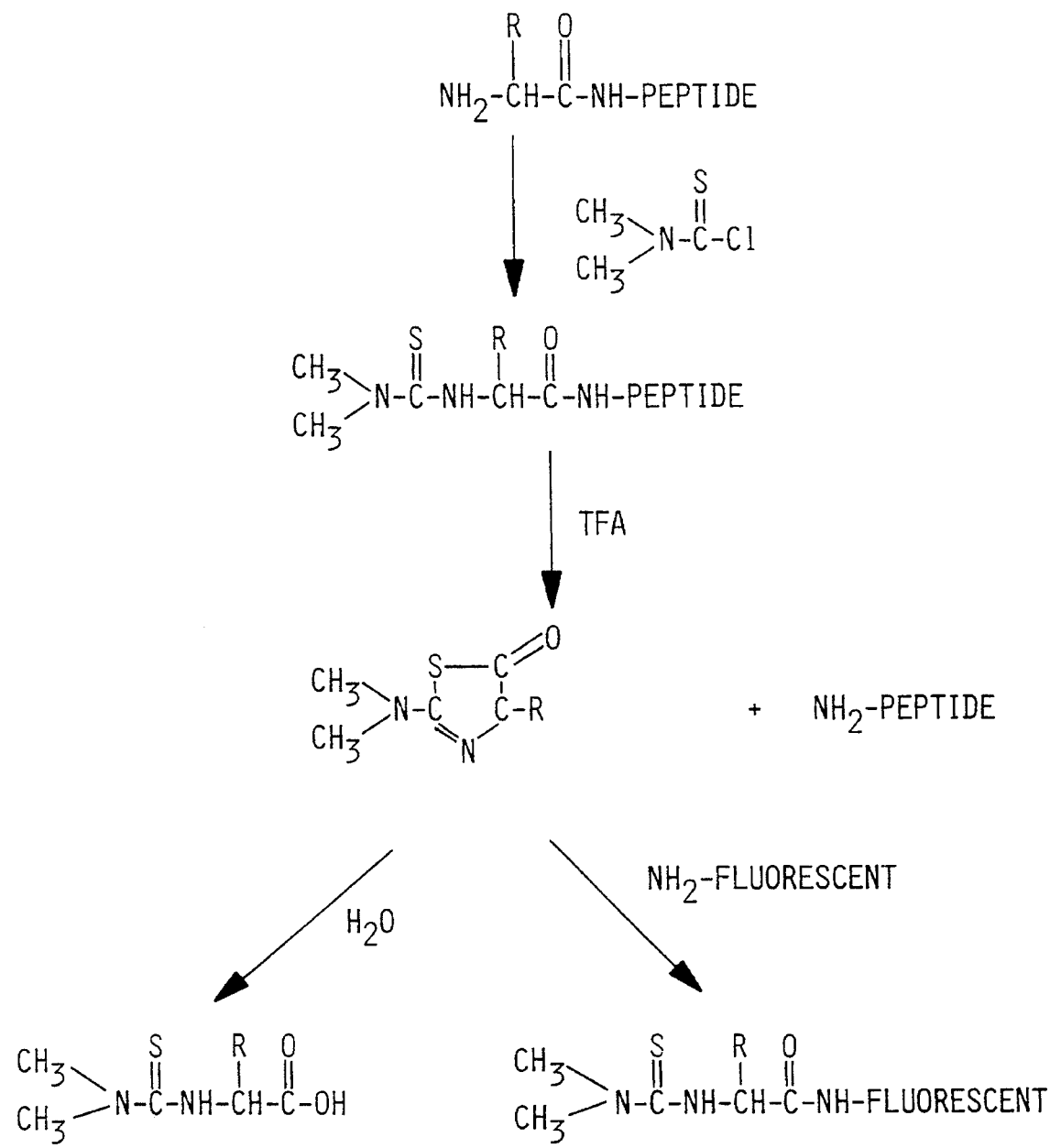
FIG. 1 is an outline of the chemistry and of the method steps representative of one embodiment of the invention.

The peptide or protein to be sequenced preferably is attached either covalently or non-covalently to a solid support of the type usually used. Such supports include, for example, polyvinylidene difluoride, polyethylene and glass.

See copending, commonly assigned applications PCT/US91/04434 and U.S. application Ser. No. 07/576,943 (describing certain solid supports for use in C-terminal sequencing which are also useful in the practice of this invention).

As depicted by FIG. 1, the peptide is first derivatized with a thiocarbamoyl reagent, as shown in the Figure, dimethylthiocarbamoyl chloride. The reaction product is then cleaved in known manner with an acid such as hydrochloric acid or with trifluoroacetic acid (TFA) to provide a cyclic dimethylthiocarbamoyl derivative of the N-terminal amino acid of the sample and the residual peptide lacking said N-terminal amino acid.

The cyclic derivative is then linearized by reaction either with water or with a fluorescent reagent. Preferred fluorescent reagents have an amino group available to react with the cyclic reagent. Such reagents specifically include 4-aminofluorescein, aminopyrene, and tetramethylrhodamine. The linear product is identified by spectroscopic or fluorescent analysis.

The thiocarbamoyl reagents useful in the invention are depicted by the formula

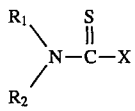

in which $R_1$ and $R_2$ may be the same or different alkyl groups having from about 1 to about 18 carbon atoms, a phenyl group or a substituted phenyl group,
and X is chlorine, bromine, fluorine or iodine, SR or OR in which R is an alkyl group having from 1 to 18 carbon atoms a phenyl group, a substituted phenyl group or a trialkylsilyl group, —N3, —CN, —NCS an alkyl or phosphoryl anhydride group.

The thiocarbamoyl reagent may be utilized either per se in solution in an inert solvent such as acetonitrile or heptane. Typically the reaction with the thiocarbamoyl reagent will take place at between 30°–80° C. for 15–45 minutes.

Preferred alkyl groups R, $R_1$ and $R_2$ have from about 1 to about 5 carbon atoms. The $R_1$ and $R_2$ groups may be either straight or branched chain. For example, the $R_1$ and $R_2$ groups may be methyl, ethyl, propyl, isopropyl, butyl, or isobutyl.

Alkyl anhydride groups useful as substituent "X" have the formula

Phosphoryl anhydride groups useful as substituent "X" have the formula

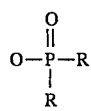

In the alkyl and phosphoryl anhydride groups "R" may also have from about 1 to about 18, preferably from 1 to 5, carbon atoms.

EXAMPLE 1

A. Reaction of Valine ethyl ester with Dimethylthiocarbamoylchloride.

Valine ethyl ester (0.0028 mol) in 10 ml acetonitrile was reacted with dimethylthiocarbamoyl chloride (0.0056 mol) at 50° C. for 2 hours. Solvent acetonitrile was removed by rotary evaporation. Trifluoroacetic acid (10 ml) was added and the mixture stirred at room temperature for 15 min. The trifluoroacetic acid was removed by rotary evaporation. The residue was dissolved in water and analyzed by FAB/MS. The expected product, dimethylthiocarbamoyl valine (MH+ =205), was obtained.

This method for N-terminal sequencing has a number of advantages over the prior art. These advantages include: (1) the simplicity of the chemistry as compared to the chemistry of the prior art, e.g., no thiohydantoin formation occurs, (2) the fact that the ATZ derivative formed is not capable of rearranging to a thiohydantoin derivative, thereby making the ATZ derivative stable until a fluorescent amine is introduced, (3) the thiocarbamoyl reagents are all ideally suited for detection by mass spectrometry by virtue of the tertiary amine group. The increased basicity of the tertiary amine functionally enhances formation of the protonated molecule which results in an increased sensitivity of detection by electrospray mass spectroscopy. This eliminates the necessity for further chemical steps later in the sequence (after the washing step) in order to introduce the tertiary amine, thereby eliminating the possibility for introduction of unwanted background peaks due to excess amine reagent, and (4) the derivatized amine acid product released during sequencing absorbs UV light at 250 nm with an extinction coefficient similar to the PTH amine acids released during the Edman degradation.

This permits three modes of detection of the released amine acid: (1) standard UV detection, permitting equivalent sensitivity as prior art, (2) detection by fluorescence (after reaction with a fluorescent reagent), permitting sub-picomole detection, and (3) detection by electrospray mass spectrometry, permitting rapid sub-picomole detection.

We claim:

1. A method for the sequential degradation of a protein or peptide sample from the N-terminus which comprises derivatizing the N-terminus of the peptide by reaction with a derivatizing reagent to form a peptidyl thiourea derivative, cleaving said derivative to provide a thiourea derivative of the amino acid previously at the N-terminus of the peptide and a peptidyl residue lacking such amino acid, whereas said derivatizing reagent is a thiocarbamoyl compound having the formula

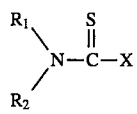

in which $R_1$ and $R_2$ may be the same or different alkyl groups having from about 1 to about 18 carbon atoms, a phenyl group or a substituted phenyl group,
and X is chlorine, bromine, fluorine oriodine, SR or OR in which R is an alkyl group having from 1 to 18 carbon atoms, a phenyl group, a substituted phenyl group or a trialkylsilyl group, —N3, —CN, —NCS an alkyl or phosphoryl anhydride group.

2. A method as defined by claim 1 in which R, $R_1$ and $R_2$ are alkyl groups having from 1 to 5 carbon atoms.

3. A method as defined by claim 1 in which the thiocarbamoyl reagent is a dialkylthiocarbamoylhalide.

4. A method for the sequential degradation of a protein or peptide sample from the N-terminus which comprises derivatizing the N-terminus of the peptide by reaction with a derivatizing reagent to form a peptidyl thiourea derivative, cleaving said derivative to provide a thiourea derivative of the amino acid previously at the N-terminus of the peptide and a peptidyl residue lacking such amino acid, wherein said derivatizing reagent is dimethylthiocarbamoyl chloride.

* * * * *